(12) United States Patent
Kurnik

(10) Patent No.: US 11,615,863 B2
(45) Date of Patent: *Mar. 28, 2023

(54) UNIVERSAL METHOD TO DETERMINE REAL-TIME PCR CYCLE THRESHOLD VALUES

(71) Applicant: Roche Molecular Systems, Inc., Pleasanton, CA (US)

(72) Inventor: Ronald T. Kurnik, Foster City, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 1142 days.

This patent is subject to a terminal disclaimer.

(21) Appl. No.: 16/203,070

(22) Filed: Nov. 28, 2018

(65) Prior Publication Data

US 2019/0095576 A1 Mar. 28, 2019

Related U.S. Application Data

(63) Continuation of application No. 13/633,813, filed on Oct. 2, 2012, now Pat. No. 10,176,293.

(51) Int. Cl.
| | | |
|---|---|---|
| *G16B 20/20* | (2019.01) | |
| *G16B 20/00* | (2019.01) | |
| *G16B 40/00* | (2019.01) | |
| *C12Q 1/6851* | (2018.01) | |
| *G16B 40/10* | (2019.01) | |
| *G06F 17/17* | (2006.01) | |
| *G06F 17/10* | (2006.01) | |

(52) U.S. Cl.
CPC .......... *G16B 20/20* (2019.02); *C12Q 1/6851* (2013.01); *G06F 17/10* (2013.01); *G06F 17/17* (2013.01); *G16B 20/00* (2019.02); *G16B 40/00* (2019.02); *G16B 40/10* (2019.02)

(58) Field of Classification Search
None
See application file for complete search history.

(56) References Cited

U.S. PATENT DOCUMENTS

| | | | |
|---|---|---|---|
| 5,373,457 A | 12/1994 | George et al. | |
| 6,303,305 B1 | 10/2001 | Wittwer et al. | |
| 6,503,720 B2 | 1/2003 | Wittwer et al. | |
| 6,783,934 B1 | 8/2004 | McMillan et al. | |
| 7,008,623 B1 | 3/2006 | Bonnefoy et al. | |
| 7,043,461 B2 | 5/2006 | Kehder | |
| 7,179,589 B2 | 2/2007 | Brookes | |
| 7,228,237 B2 | 6/2007 | Woo et al. | |
| 7,668,663 B2 | 2/2010 | Kurnik et al. | |
| 7,680,604 B2 | 3/2010 | Kurnik | |
| 7,680,868 B2 | 3/2010 | Kurnik et al. | |
| 7,788,039 B2 | 8/2010 | Vess | |
| 7,991,561 B2 | 8/2011 | Kurnik | |
| 7,991,562 B2 | 8/2011 | Kurnik et al. | |
| 8,219,324 B2 | 7/2012 | Kurnik | |
| 8,219,366 B2 | 7/2012 | Kurnik | |
| 2006/0009916 A1 | 1/2006 | Li et al. | |
| 2007/0143070 A1 | 6/2007 | Kurnik et al. | |
| 2007/0143385 A1 | 6/2007 | Kurnik et al. | |
| 2007/0148632 A1 | 6/2007 | Kurnik et al. | |
| 2008/0033701 A1 | 2/2008 | Kurnik | |
| 2009/0119020 A1 | 5/2009 | Kurnik | |
| 2009/0287754 A1 | 11/2009 | Sane et al. | |
| 2010/0070185 A1 | 3/2010 | Kurnik et al. | |
| 2011/0054852 A1 | 3/2011 | Titz et al. | |

FOREIGN PATENT DOCUMENTS

| | | |
|---|---|---|
| CN | 1987880 A | 6/2007 |
| EP | 1801706 A2 | 6/2007 |
| EP | 1804172 A2 | 7/2007 |
| EP | 2163999 A2 | 3/2010 |
| JP | 2002-514421 | 5/2002 |
| WO | 97/46707 A2 | 12/1997 |
| WO | 97/46712 A2 | 12/1997 |
| WO | 97/46714 A1 | 12/1997 |
| WO | 2006/124673 A2 | 11/2006 |
| WO | 2003/067215 A2 | 6/2007 |
| WO | 2011/131490 A2 | 10/2011 |

OTHER PUBLICATIONS

Guescini, M., et al., "A new real-time PCR method to overcome significant quantitative inaccuracy due to slight amplification inhibition," BCM Bioinformatics, [online], Jul. 30, 2008, vol. 9, No. 326, 12 pages, retrieved from URL: http://www.biomedcentral.com.
Guescini, M., et al., "Accurate and Precise DNA Quantification in the Presence of Different Amplification Efficiencies Using an Improved Cy0 Method," PLOS One, Jul. 8, 2013, vol. 8, No. 7, 11 pages.
Chandrasekaran, et al., "Summarizing data through a piecewise linear growth curve model", Statistics in Medicine, Apr. 2005, vol. 24, Issue 8, pp. 1139-1151.
Lei et al., "Comparison and selection of growth models using the Schnute model", Journal of Forest Science, 52, 2006 (4), pp. 188-196.
Cogger, "Piecewise Linear Modeling: Theory, Guidelines, and Applications", Management Science & Technology Symposium, University of Kansas School of Business, Mar. 2006.
Hu, "Akaike Information Criterion", Center for Research in Scientific Computation, North Carolina State University, Mar. 2007, 19 pages.
Bieche, I. et al., "Quantitation of MYC Gene Expression in Sporadic Breast Tumors with a Real-Time Reverse Transcription-PCR Assay," Cancer Research, Jun. 15, 1999, vol. 59, pp. 2759-2765.
Gibson, U.E.M. et al., "A Novel Method for Real Time Quantitative RT-PCR," Genome Research, 1996, vol. 6, pp. 995-1001.

(Continued)

*Primary Examiner* — Joseph Woitach
(74) *Attorney, Agent, or Firm* — Kilpatrick Townsend & Stockton LLP

(57) ABSTRACT

A single technique for determining Ct is provided that can be used for standard sigmoidal growth curves and for problematic growth curves, such as parabolic curves. The Ct value can be determined as the intersection of a line tangent to the growth curve at the maximum of the second derivative with a baseline of the growth curve. Such a Ct value is usable for sigmoidal curves and parabolic curves, and can provide linear calibration curves to achieve accuracy in determining initial concentrations of a sample.

20 Claims, 10 Drawing Sheets

(56) References Cited

OTHER PUBLICATIONS

Wang, S-S. et al., "Homogenous Real-Time Detection of Single-Nucleotide Polymorphisms by Strand Displacement Amplification on the BD ProbeTec ET System," Clinical Chemistry, 2003, vol. 49, No. 10, pp. 1599-1607.

Weusten, J.J.A.M. et al., "Principles of quantitation of viral loads using nucleic acid sequence-based amplification in combination with homogenous detection using molecular beacons," Nucleic Acids Research, 2002, vol. 30, No. 6, e26, pp. 1-7.

Aguirre-Hernandez, Rosalia, et al., "Computational RNA secondary structure design: empirical complexity and improved methods," BMC Bioinformatics, 2007, 16 pages.

Wilhelm, et al., "SoFAR: Software for fully automatic evaluation of real-time PCR Data," BioTechniques, 2003, vol. 34, pp. 324-332.

Karlen, et al., "Statistical significance or quantitative PCR," BMC Bioinformatics, 2007, vol. 8, pp. 1-16.

Tichopad et al., Improving Quantitative Real-Time RT-PCR Reproducibility by Boosting Primer-Linked Amplification Efficiency, Biotechnology Letters 2002, pp. 2053-2056, vol. 24, Kluwer Academic Publishers, The Netherlands.

Kacena et al., Bacterial Growth in Space Flight: Logistic Growth Curve Parameters for *Excherichia coli* and *Bacillus subtilis*, Applied Microbiology and Biotechnology, 1999, pp. 2-7, vol. 51, Issue 2, Springer-Verlag.

Bassukas, Use of the Recursion Formula of the Gompertz Survival Function to Evaluate Life-Table Data, Mechanisms of Aging and Development, 1996, pp. 155-163, vol. 89, Elsevier Science, Ireland.

Cambridge University Press, "Root Finding and Nonlinear Sets of Equations," Chapter 9 in Numerical Recipes in C: The Art of scientific Computing, 1988-1992, pp. 347-369.

Kurnik, R.T. et al., "Application of the Mixtures of Experts Algorithm for Signal Processing in a Noninvasive Glucose Monitoring System," Sensors and Actuators B, 1999, vol. 60, pp. 19-26.

Lourakis, M.I.A., "A Brief Description of the Levenberg-Marquardt Algorithm Implemened by levmar," Feb. 11, 2005, pp. 1-6.

McLauchlan, P., "Robust Observations," located at <http://gandalf-library.sourceforge.net/tutorial/report/node131.html>, Mar. 17, 2006, last visited on Jan. 25, 2008, two pages.

Motulsky, H. et al., Fitting Models to Biological Data Using Linear and Nonlinear Regression, Version 4.0, GraphPad Software, Inc., 2003, pp. 3-11 (Table of Contents Only).

Motulsky, H., Statistics Guide Statistical Analyses for Laboratory and Clinical Researchers, Version 4.0, GraphPad Software, Inc., Feb. 2005, six pages (Table of Contents Only).

Weisstein, E., "Cubic Spline," located at <http://mathwolrd.wolfram.com/CubicSpline.html>, 1999, last visited on Jan. 25, 2008, four pages.

FIG. 1A
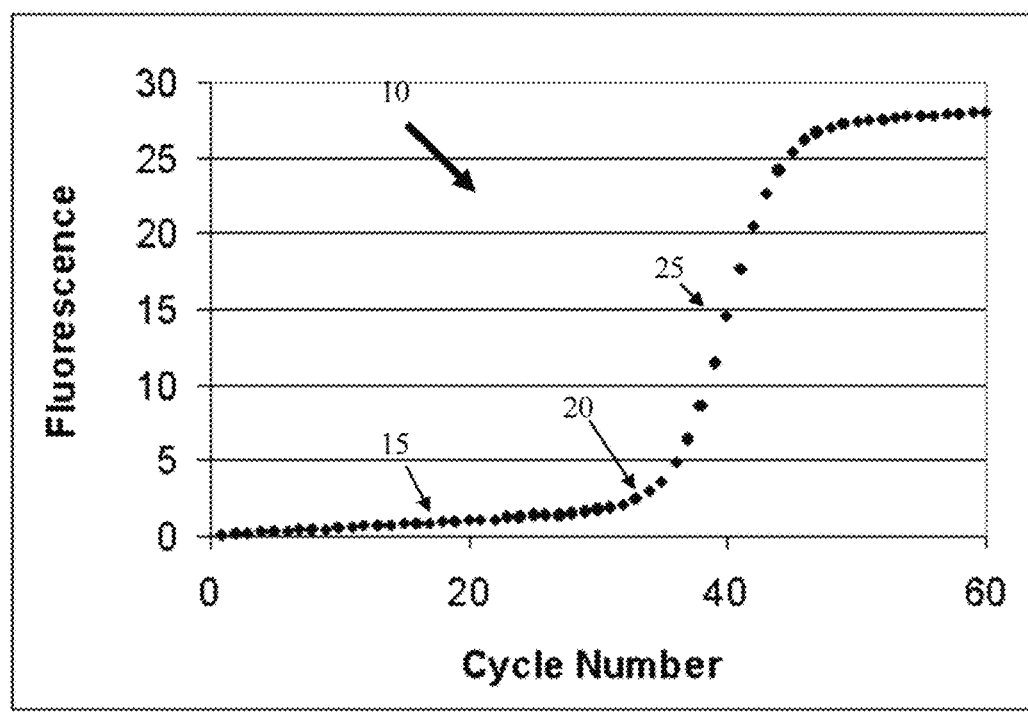
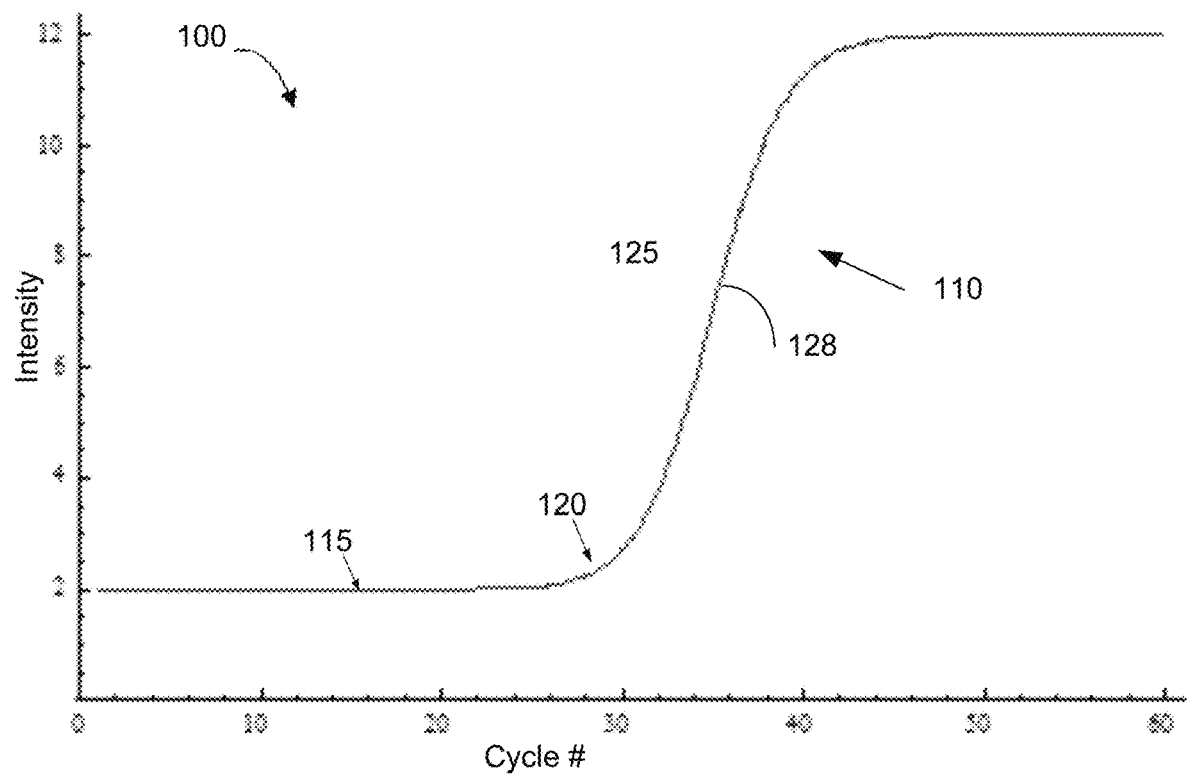
FIG. 1B

UNIVERSAL METHOD TO DETERMINE REAL-TIME PCR CYCLE THRESHOLD VALUES

CROSS-REFERENCES TO RELATED APPLICATIONS

The present application is a continuation of U.S. patent application Ser. No. 13/633,813, filed Oct. 2, 2012, entitled "Universal Method to Determine Real-time PCR Cycle Threshold values," the content of which is herein incorporated by reference in its entirety for all purposes.

BACKGROUND

The present disclosure relates generally to systems and methods for processing data representing sigmoid or growth curves, and more particularly to systems and methods for determining characteristic cycle threshold (Ct) or elbow values in real-time Polymerase Chain Reaction (PCR) amplification curves, or elbow values in other growth curves.

The Polymerase Chain Reaction is an in vitro method for enzymatically synthesizing or amplifying defined nucleic acid sequences. The reaction typically uses two oligonucleotide primers that hybridize to opposite strands and flank a template or target DNA sequence that is to be amplified. Elongation of the primers is catalyzed by a heat-stable DNA polymerase. A repetitive series of cycles involving template denaturation, primer annealing, and extension of the annealed primers by the polymerase results in an exponential accumulation of a specific DNA fragment. Fluorescent probes or markers are typically used in the process to facilitate detection and quantification of the amplification process A typical kinetic PCR curve is shown in FIG. 1A, where fluorescence intensity values are plotted vs. cycle number for a typical PCR process. In this case, the formation of PCR products is monitored in each cycle of the PCR process. The amplification is usually measured in thermocyclers which include components and devices for measuring fluorescence signals during the amplification reaction. An example of such a thermocycler is the Roche Diagnostics LightCycler (Cat. No. 20110468). The amplification products are, for example, detected by means of fluorescent labeled hybridization probes which only emit fluorescence signals when they are bound to the target nucleic acid or in certain cases also by means of fluorescent dyes that bind to double-stranded DNA.

For a typical PCR curve, identifying a transition point at the end of the baseline region, which is referred to commonly as the elbow value or cycle threshold (Ct) value, is extremely useful for understanding characteristics of the PCR amplification process. The Ct value may be used as a measure of efficiency of the PCR process. For example, typically a defined signal threshold is determined for all reactions to be analyzed and the number of cycles (Ct) required to reach this threshold value is determined for the target nucleic acid as well as for reference nucleic acids such as a standard or housekeeping gene. The absolute or relative copy numbers of the target molecule (starting material) can be determined on the basis of the Ct values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714). The elbow value 20 at the end of the baseline region 15 in FIG. 1A would be in the region of cycle number 30.

The elbow value in a PCR curve can be determined using several existing methods. For example, various methods determine the actual value of the elbow (Ct) as the value where the fluorescence on a normalized PCR curve reaches a predetermined signal level, called the AFL (arbitrary fluorescence value), which can be sensitive to changes in the average baseline fluorescent level in the pre-elbow PCR cycles. Other methods use the cycle number where the second derivative of fluorescence vs. cycle number reaches a maximum, which can give late Ct values, particularly for parabolic curves. Yet other methods use a tangent of the PCR curve at the inflection point (maximum of first derivative), which is problematic for parabolic curves as the maximum of the first derivative may not exist. (Guescini, BMC Bioinformatics, 9:326, 2008). Thus, the latter two methods both have drawbacks for parabolic curves. U.S. Pat. No. 8,219,366 solves the problem with parabolic curves by identifying such curves and using a different technique for such problematic curves. Although this method works well for qualitative real-time PCR, when applied to quantitative real-time PCR, it can lead to some increase in imprecision at low copy numbers.

Therefore it is desirable to provide systems and methods for determining Ct value in growth curves, such as real-time PCR amplification curves or other growth curves, which overcome the above and other problems.

BRIEF SUMMARY

Systems, methods, and apparatuses are provided for determining a Ct according to one technique that is applicable to various experimental conditions. A single technique for determining Ct can be used for standard sigmoidal growth curves and for problematic growth curves, such as parabolic curves. The Ct value can be determined as the intersection of a line tangent to the growth curve at the maximum of the second derivative with a baseline of the growth curve. Such a Ct value is usable for sigmoidal curves and parabolic curves, and can provide linear calibration curves to achieve accuracy in determining initial concentrations.

For example, embodiments can determine the slope and signal value of a double sigmoid fit (i.e. to the raw data points of a PCR curve) at the second derivative maximum. This slope and signal value are sufficient to draw a straight line that intersects the baseline of the PCR curve. This intersection point can then be defined as the Ct value.

According to one embodiment, a method determines a cycle threshold value Ct in a growth curve of a growth process. A dataset representing a growth curve is received. The dataset includes a plurality of data points. Each data point has a pair of coordinate values of a cycle number and a signal strength of the growth process at the cycle number. A function that approximates the dataset is calculated. A baseline of the growth curve is determined, where the baseline is linear. A computer system computes a first point of the function where a maximum in a second derivative of the function occurs. The computer system determines a tangent line that is tangent to the function at the first point. The computer system computes an intersection point of the tangent line and the baseline, where the cycle number of the intersection point is the cycle threshold value Ct.

Other embodiments are directed to systems and computer readable media associated with methods described herein.

A better understanding of the nature and advantages of the present invention may be gained with reference to the following detailed description and the accompanying drawings.

BRIEF DESCRIPTION OF THE DRAWINGS

FIG. 1A illustrates an example of a typical PCR growth curve, plotted as fluorescence intensity vs. cycle number.

FIG. 1B is a simulated real-time PCR curve according to embodiments of the present invention.

DETAILED DESCRIPTION

Figure 2A:
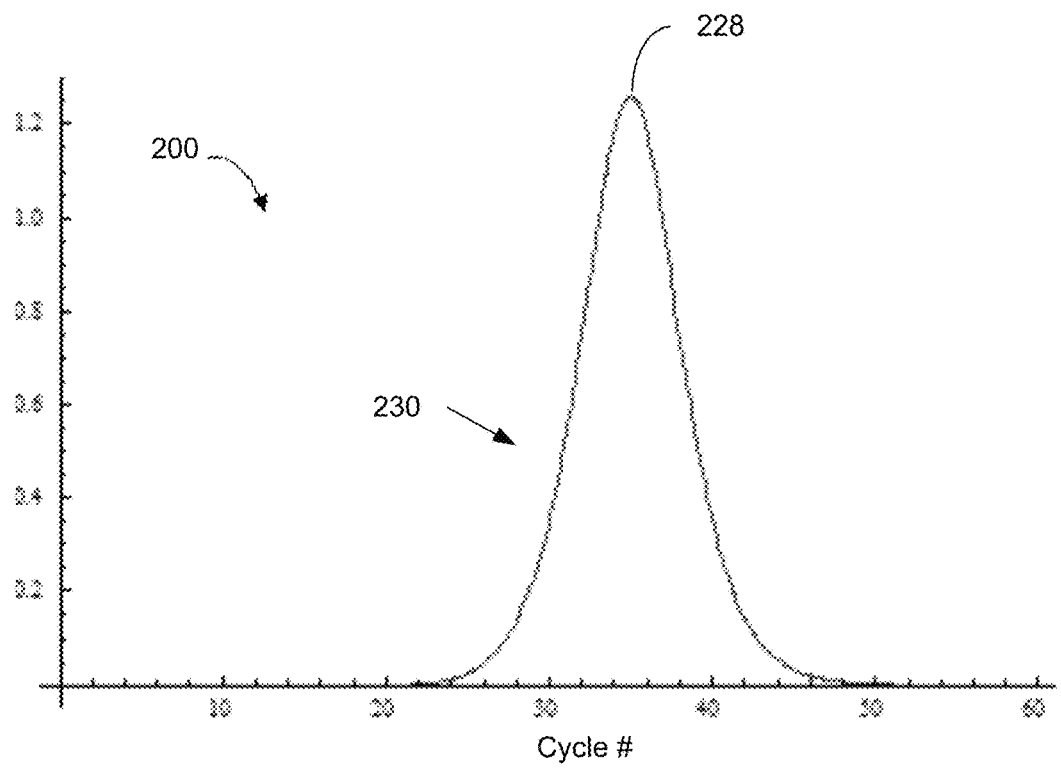
FIG. 2A shows a plot 200 of the first derivative 230 of PCR curve 110 according to embodiments of the present invention.

Growth curves (e.g., real-time Polymerase Chain Reaction (PCR) curves) of a sample can be analyzed to determine an initial concentration. Typically, a cycle threshold Ct (also called an elbow value) is used as a proxy for the initial concentration, where a calibration curve can be used to determine a corresponding initial concentration from a measured Ct. However, it can be difficult to determine consistent Ct values, as certain growth (amplification) curves can be problematic. One can use different techniques for these problematic curves, but doing so can compromise the calibration curve and the ability to properly quantify the initial concentration.

Embodiments of the present invention provide a single technique for determining Ct that can be used for standard sigmoidal growth curves and for problematic growth curves, such as parabolic curves. The Ct value can be determined as the intersection of a line tangent to the growth curve at the maximum of the second derivative with a baseline of the growth curve. Such a Ct value is usable for sigmoidal curves and parabolic curves, and can provide linear calibration curves to achieve accuracy in determining initial concentrations. An initial description of a real-time PCR curve is first provided.

I. General Overview

One example of an amplification curve 10 in the context of a kinetic PCR process is shown in FIG. 1A. As shown, the curve 10 includes a lag phase region 15, and an exponential phase region 25. Lag phase region 15 is commonly referred to as the baseline or baseline region. Such a curve includes a transition region 20 linking the lag phase and the exponential phase. Region 20 is commonly referred to as the elbow or elbow region. The elbow region typically defines an end to the baseline and a transition in the growth or amplification rate of the underlying process. Identifying a specific transition point in region 20 can be useful for analyzing the behavior of the underlying process.

In a typical PCR curve, identifying a transition point referred to as the elbow value or cycle threshold (Ct) value is extremely useful for understanding efficiency characteristics of the PCR process. For example, the Ct value can be used to provide quantization of the amount of DNA present in the sample being analyzed. Quantization is obtained by performing a calibration curve of the Log(DNA Amount) vs. Ct value. Subsequent samples can then use Ct values along with the calibration curve to directly obtain estimates of DNA in a sample. Ct values can also be used to provide qualitative information on the DNA sample.

Other processes that may provide similar sigmoid or growth curves include bacterial processes, enzymatic processes and binding processes. In bacterial growth curves, for example, the transition point of interest has been referred to as the time in lag phase, $\lambda$. Other specific processes that produce data curves that may be analyzed according to the present invention include strand displacement amplification (SDA) processes, nucleic acid sequence-based amplification (NASBA) processes and transcription mediated amplification (TMA) processes. Examples of SDA and NASBA processes and data curves can be found in Wang, Sha-Sha, et al., "Homogeneous Real-Time Detection of Single-Nucleotide Polymorphisms by Strand Displacement Amplification on the BD ProbeTec ET System," Clin Chem 2003 49(10):1599, and Weusten, Jos J. A. M., et al., "Principles of Quantitation of Viral Loads Using Nucleic Acid Sequence-Based Amplification in Combination With Homogeneous Detection Using Molecular Beacons," Nucleic Acids Research, 2002 30(6):26, respectively, both of which are hereby incorporated by reference. Thus, although the remainder of this document will discuss embodiments and aspects of the invention in terms of its applicability to PCR curves, it should be appreciated that the present invention may be applied to data curves related to other processes.

As shown in FIG. 1A, data for a typical PCR growth curve can be represented in a two-dimensional coordinate system, for example, with PCR cycle number defining the x-axis and an indicator of accumulated polynucleotide growth defining the y-axis. Typically, the indicator of accumulated growth is a fluorescence intensity value as the use of fluorescent markers is perhaps the most widely used labeling scheme. However, it should be understood that other indicators may be used depending on the particular labeling and/or detection scheme used. Examples of other useful indicators of accumulated signal growth include luminescence intensity, chemiluminescence intensity, bioluminescence intensity, phosphorescence intensity, charge transfer, voltage, current, power, energy, temperature, viscosity, light scatter, radioactive intensity, reflectivity, transmittance, and absorbance. All such examples fall under a signal strength. The definition of a cycle can also include time, process cycles, unit operation cycles and reproductive cycles.

II. Determining Ct Value

Embodiments use the intersection of a line tangent to the growth curve at the maximum of the second derivative with a baseline of the growth curve. To obtain the point of the maximum of the second derivative of a growth curve, one can obtain a functional approximation (curve fit) to the data points of the particular growth process (e.g., real-time PCR). A second derivative of the function can be computed and analyzed to determine at what cycle (xval) the maximum occurs. The tangent line can then be determined based on the slope of the function at xval. After a baseline of the function is determined, the intersection of the tangent line and the baseline can be calculated. The Ct value is then returned and may be displayed or otherwise used for further processing. Such a Ct value is usable for sigmoidal curves and parabolic curves, and can provide linear calibration curves to achieve accuracy in determining initial concentrations. Simulated growth curves are now used to illustrate embodiments.

FIG. 1B shows a plot 100 with a simulated real-time PCR curve 110 according to embodiments of the present invention. PCR curve 110 has cycle number on the horizontal (x) axis and intensity (e.g., fluorescence) on the vertical (y) axis. PCR curve 110 has a well-defined baseline 115. As shown, baseline 115 is a horizontal line at intensity (y) equal to two. For ease of presentation, there is no slope to simulated baseline 115. However, a baseline may have any linear form with a slope. Elbow region 120 lies between baseline 115 and exponential phase region 125. Exponential phase region 125 includes inflexion point 128 where PCR curve 110 begins to curve downward, as opposed to upward in elbow region 120.

Although PCR growth curve 110 is simulated, a PCR growth curve can be determined from data points of intensity taken at each cycle. A particular functional form can be assumed, and parameters can be determine such that the particular functional form approximates the data point. In some embodiments, a double sigmoid function with parameters determined by a Levenberg-Marquardt (LM) regression process can be used to find an approximation to the data points. In other embodiments, other functional forms may be used, e.g., interpolation using polynomials with continuous boundary conditions (e.g., continuous up to the second derivative) as may occur in finite element analysis, a single sigmoid function, or any set of one or more functions with a continuous second derivative across the regions of interest. In one aspect, the curve approximation and parameters can be used to pre-process the data signal, e.g., to normalize the data signal and/or to remove spikes or outlier data points as may be present in the data signal.

FIG. 2A shows a plot 200 of the first derivative 230 of PCR curve 110 according to embodiments of the present invention. The x-axis is still cycle number, but the y-axis is in units of change in intensity per cycle, as plot 200 shows the first derivative. First derivative 230 may be determined by taking the first derivative of the function that resulted from a curve fitting process to the data points. As shown, first derivative 230 has a maximum at inflexion point 228 (which corresponds to inflexion point 128).

Figure 2B:
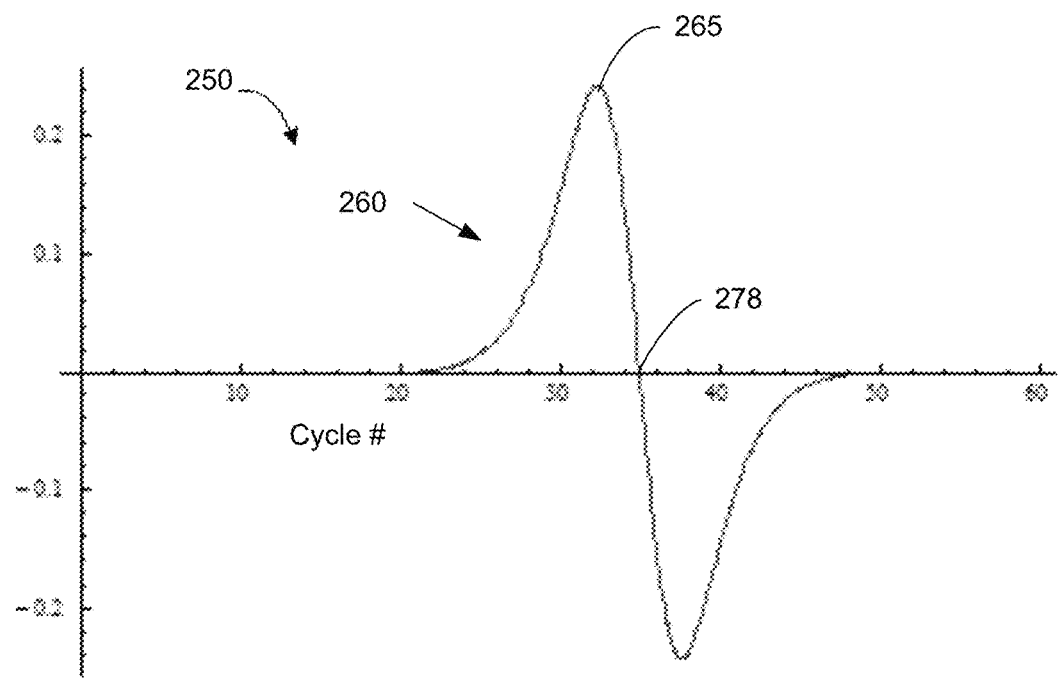
FIG. 2B shows a plot 250 of the second derivative 260 of PCR curve 110 according to embodiments of the present invention.

FIG. 2B shows a plot 250 of the second derivative 260 of PCR curve 110 according to embodiments of the present invention. Second derivative 230 may be determined by taking the second derivative of the function that resulted from a curve fitting process to the data points. The inflexion point is shown as point 278, which corresponds to where second derivative 260 is zero. Second derivative 260 has a maximum at point 265, which occurs at cycle xval. In FIG. 2B, xval equals 32.36. The maximum can be found in a variety of ways, e.g., by searching along the values of second derivative 260 or by determining zeros of a third derivative. As one can see, $2^{nd}$ derivative maximum 265 occurs before inflexion point 278.

Once xval is determined, then a slope of the PCR curve at cycle xval can be determined. In one embodiment, the slope can be determined by taking the value of the first derivative at cycle xval. A line with this slope passing through the point of the maximum second derivative can then provide a line tangent to the PCR curve at cycle xval.

Figure 3:
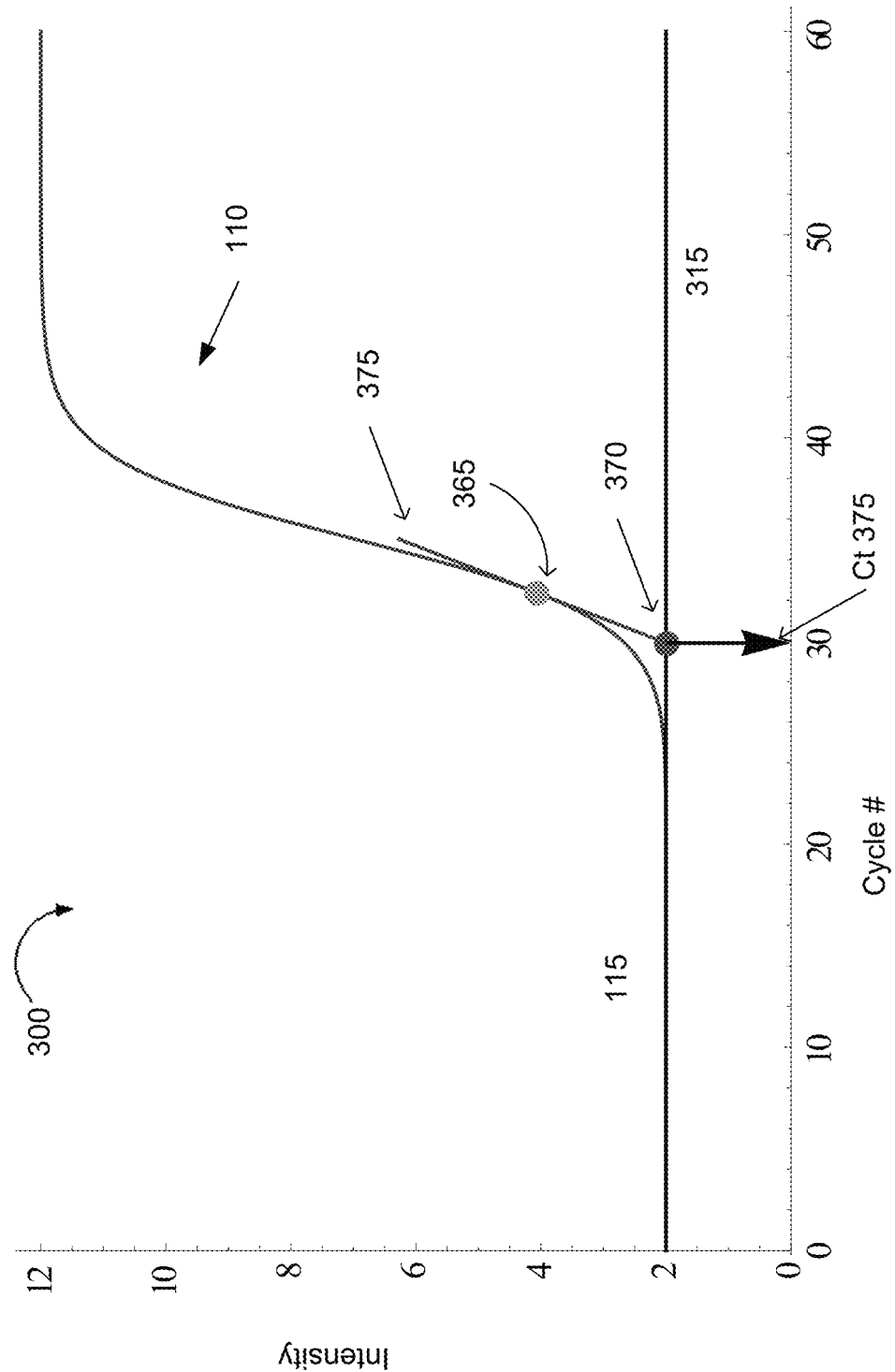
FIG. 3 shows a plot 300 with a simulated real-time PCR curve 110 illustrating a determination of Ct 375 according to embodiments of the present invention

FIG. 3 shows a plot 300 with a simulated real-time PCR curve 110 illustrating a determination of Ct 375 according to embodiments of the present invention. The point 365 on PCR curve 110 corresponds to the point of the maximum of the second derivative. Thus, point 365 occurs at the same cycle xval as point 265, which is 32.36. The slope of PCR curve 110 at xval (32.36) equals 0.8375. The intensity of PCR curve 110 at xval (32.36) equals 4.05 (yval). The equation of the line going through (xval, yval) with the given slope (0.8375) is: line(x)=yval+slp (x−xval)=0.8375 x−23.04. Tangent line 375 follows this equation.

Baseline 115, which is at y=2, is shown extended as line 315. The intersection 370 of tangent line 375 with the baseline 315 can be determined by solving the following equation for x: 0.8375 x−23.04=2 (i.e. where equation for tangent line equals equation for baseline, which may also have form of ax+b). The intersection has a solution of x=29.9, which is taken as the Ct value 375, as indicated by a down arrow to the point on the x-axis where intersection 370 occurred. A benefit of using point 365 for determining tangent line 375 is that point 365 appears in the elbow region of PCR curve 110. Thus, intersection 370 would also appear in the elbow region.

III. Method

Figure 4:
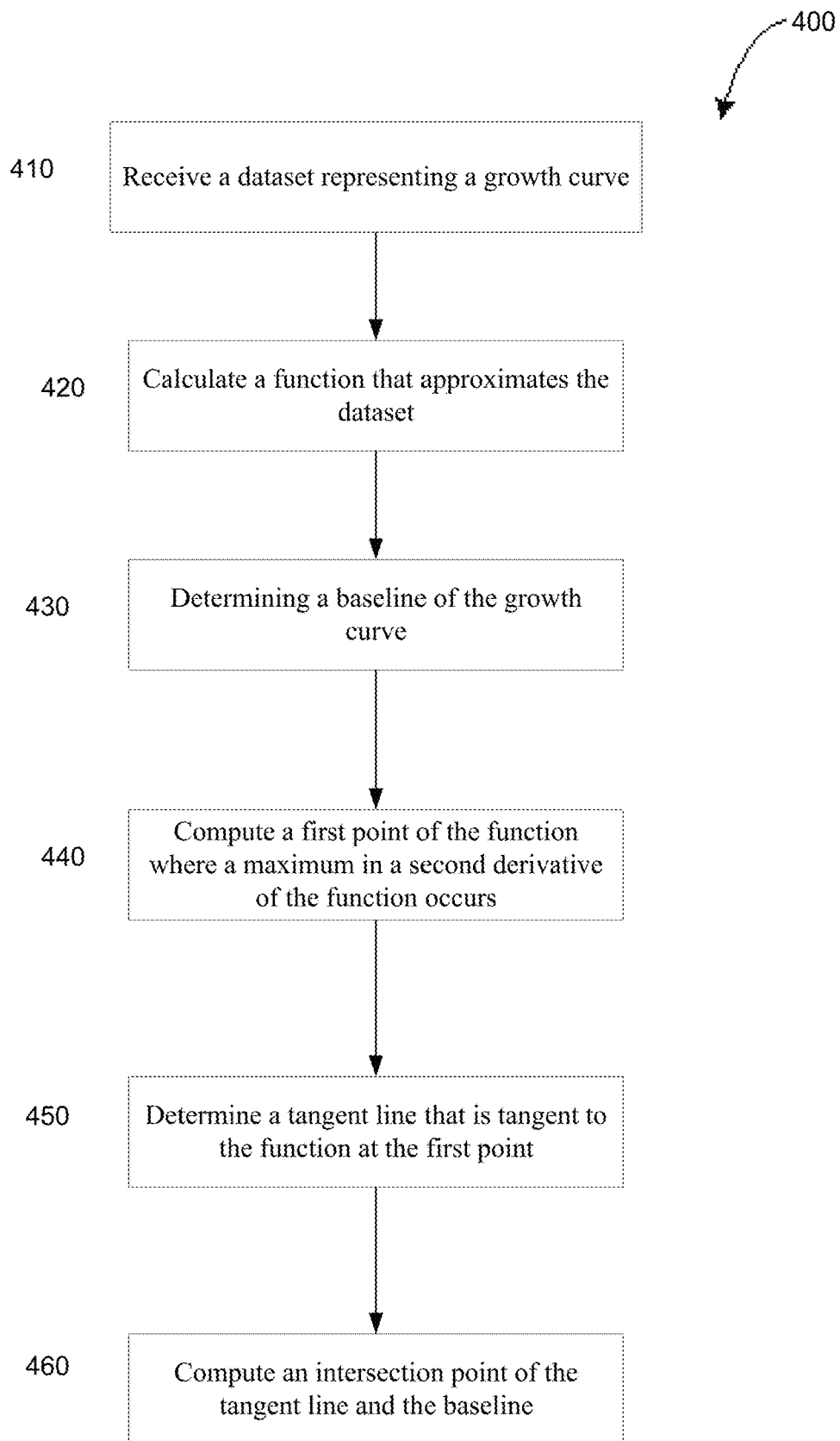
FIG. 4 is a flowchart illustrating a method 400 of determining a cycle threshold value Ct in a growth curve of a growth process.

FIG. 4 is a flowchart illustrating a method 400 of determining a cycle threshold value Ct in a growth curve of a growth process. Method 400 can be computed by a computer system. An examples growth process is real-time PCR amplification. Other growth processes include bacterial processes, enzymatic processes and binding processes. Growth processes can be measured by a series of points, with each data point providing a signal strength at a cycle number.

At block 410, a dataset representing a growth curve is received. The dataset includes a plurality of data points. Each data point has a pair of coordinate values {a cycle number, a signal strength of the growth process at the cycle number}. For example, each data point in FIG. 1A is designated by a fluorescence intensity and a cycle number. Other types of signal strengths, including other types of intensities, are mentioned herein.

At block 420, a computer system can calculate a function that approximates the dataset. This function can be determined using a regression technique to identify a best fit to the dataset. The function can have a predetermined functional form with variable parameters, and the fitting process determine the parameters. In one implementation, a double sigmoid functional form is used, which can provide an accurate function so as to allow an accurate determination of the first and second derivative.

In one embodiment, a computer system determines the best fit of the double sigmoid equation shown in equation (1) below.

$$a + bx + \frac{c}{(1 + \text{Exp}[-d(x-e)]) \cdot (1 + \text{Exp}[-f(x-g)])} \quad (1)$$

For example, a double sigmoid Levenberg-Marquardt (DSLM) curve fit can be performed as disclosed in U.S. Pat. No. 7,680,868 ("PCR Elbow Determination by Use of a Double Sigmoid Function Curve Fit with the Levenberg-Marquardt Algorithm and Normalization"), which is hereby incorporated by reference in its entirety. In one embodiment, certain data points may be removed before performing the curve fit, e.g., points at the beginning or at the Growth curve. Various implementations and processing of the double sigmoid equation have been introduced, for example the DSLM (double sigmoid Levenberg-Marquardt) equation, the DSLM with options for baseline subtraction (BLS), baseline division (BLD), and baseline subtraction with division (BLSD), the Curvature equation and others as described in U.S. application Ser. No. 11/316,315, filed Dec. 20, 2005; U.S. application Ser. No. 11/458,644, filed Jul. 19, 2006; U.S. application Ser. No. 11/533,291, filed Sep. 19, 2006; and U.S. application Ser. No. 11/861,188, filed Sep. 25, 2007, the disclosures of which are each hereby incorporated by reference for all purposes.

At block 430, a baseline of the growth curve is determined. For example, baseline 15 of FIG. 1A can be determined from the data points. The end of the baseline can be determined in various ways, e.g., by determining when the growth curve enters an exponential region. The data points corresponding to the baseline can be fit to a linear function to determine the baseline. As another example, the functional fit can be used to determine the baseline. Equation (1) includes a linear part (ax+b), which can be used to define the baseline.

At block 440, the computer system can compute a first point of the function where a maximum in a second derivative of the function occurs. For example, the computer system can determine the (xval) and (yval) positions corresponding to the maximum of the second derivative of equation (1). The xval of the second derivative can be computed, for example, as described for FIG. 2B. The yval can then be determined from xval using the functional fit.

At block 450, the computer system can determine a tangent line that is tangent to the function at the first point. In one embodiment, the slope (slp) of the functional fit (e.g., as determined using equation (1)) is determined at the first point (xval, yval). The tangent line can then be determined using the equation:

$$\text{line}(x) = yval + slp(x - xval). \quad (2)$$

At block 460, the computer system can compute an intersection point of the tangent line and the baseline, where the cycle number of the intersection point is the cycle threshold value Ct. The tangent line can be defined as above with line (x) and the baseline by ax+b, as can be determined in various ways, such as from equation (1). In one implementation, the following equation can be solved for x, where the values a and b are the values from equation (1)

$$(a + bx) = yval + slp(x - xval) \quad (3)$$

which, has the solution $$Ct = x = \frac{a + slp \cdot xval - yval}{slp - b}. \quad (4)$$

In the case where process 400 is implemented in an intelligence module (e.g., processor executing instructions) resident in a PCR data acquiring device such as a thermocycler, the data set may be provided to the intelligence module in real time as the data is being collected, or it may be stored in a memory unit or buffer and provided to the intelligence module after the experiment has been completed. Similarly, the data set may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data set includes data points having a pair of coordinate values (or a 2-dimensional vector). For PCR data, the pair of coordinate values typically represents the cycle number and the fluorescence intensity value.

IV. Scale Invariance

It is beneficial to have a technique for determination of Ct to be in a scale invariant manner for the following reasons. Different PCR machines can have different lamp intensities, length of optical fiber, and thermal cyclers, all of which can act as a multiplier on fluorescent intensity. Thus, the precise data points may depend on the machine, but ideally the determination of Ct should not depend on the variability among machines. The following figures show scale invariance of embodiments.

Figure 5A:
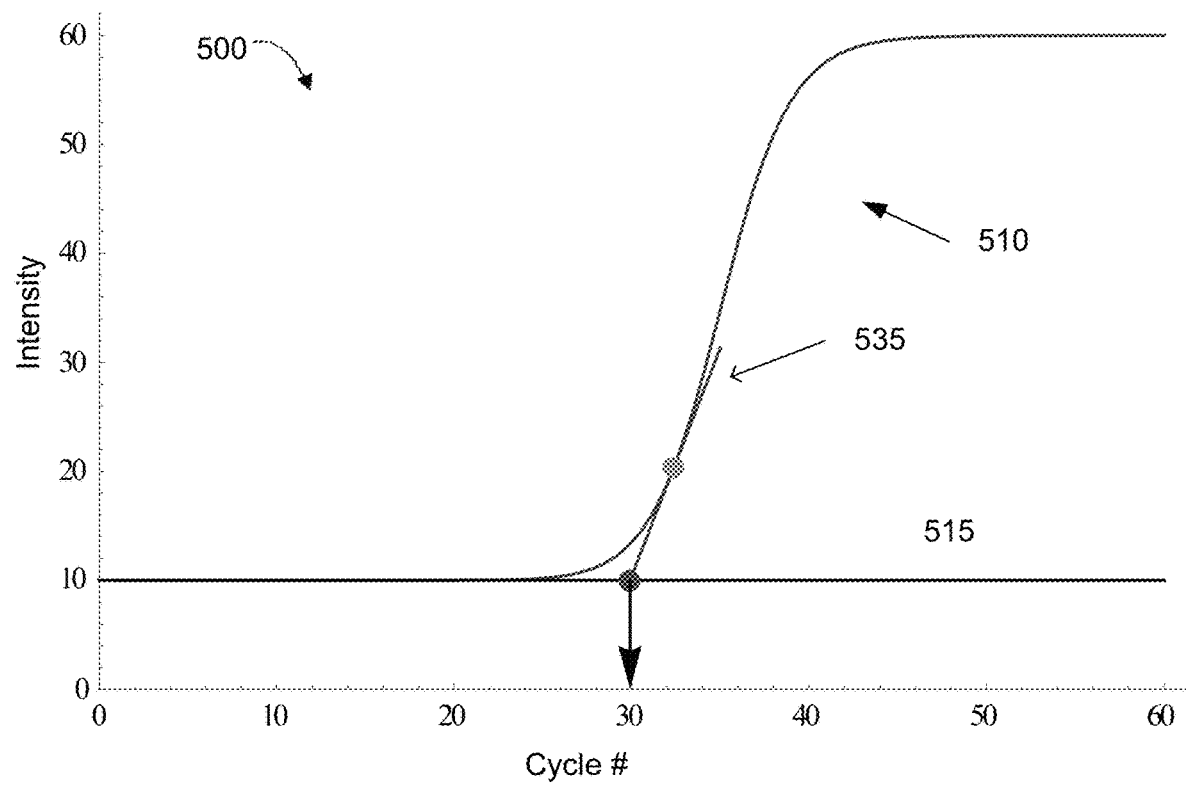
FIG. 5A shows a plot 500 for a PCR curve 510 scaled by 5 from PCR curve 110 according to embodiments of the present invention.

FIG. 5A shows a plot 500 for a PCR curve 510 scaled by 5 from PCR curve 110 according to embodiments of the present invention. PCR curve 510 is the same as PCR curve 110 except being multiplied by 5. As shown, the tangent line 535 at the maximum of the second derivative intersects with the baseline 515 at the same cycle number (29.9) as determined in FIG. 3 for PCR curve 110. Thus, even if the PCR curve is multiplied by a constant (e.g., due to using a different machine), then one gets the same Ct.

Figure 5B:
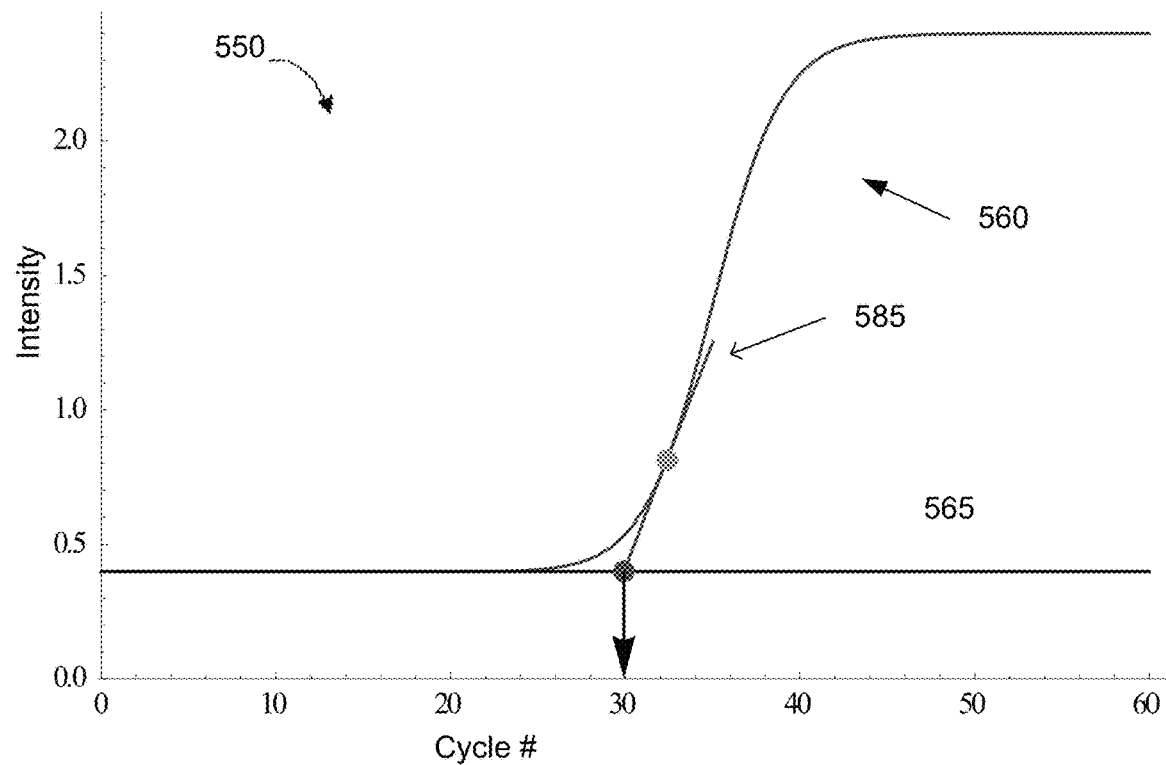
FIG. 5B shows a plot 500 for a PCR curve 510 scaled by ⅕ from PCR curve 110 according to embodiments of the present invention.

FIG. 5B shows a plot 500 for a PCR curve 510 scaled by ⅕ from PCR curve 110 according to embodiments of the present invention. PCR curve 560 is the same as PCR curve 110 except being divided by 5. As shown, the tangent line 585 at the maximum of the second derivative intersects with the baseline 565 at the same cycle number (29.9) as determined in FIG. 3 for PCR curve 110. Thus, even if the PCR curve is divided by a constant (e.g., due to using a different machine), then one gets the same Ct.

V. Parabolic Curves

As mentioned above, parabolic curves are problematic for certain techniques for calculating Ct. For example, an inflexion point (maximum of first derivative and zero of second derivative) is not always available. Additionally, using a maximum of the second derivative can provide poor results. However, embodiments of the present invention can reliably provide better Ct values.

Figure 6A:
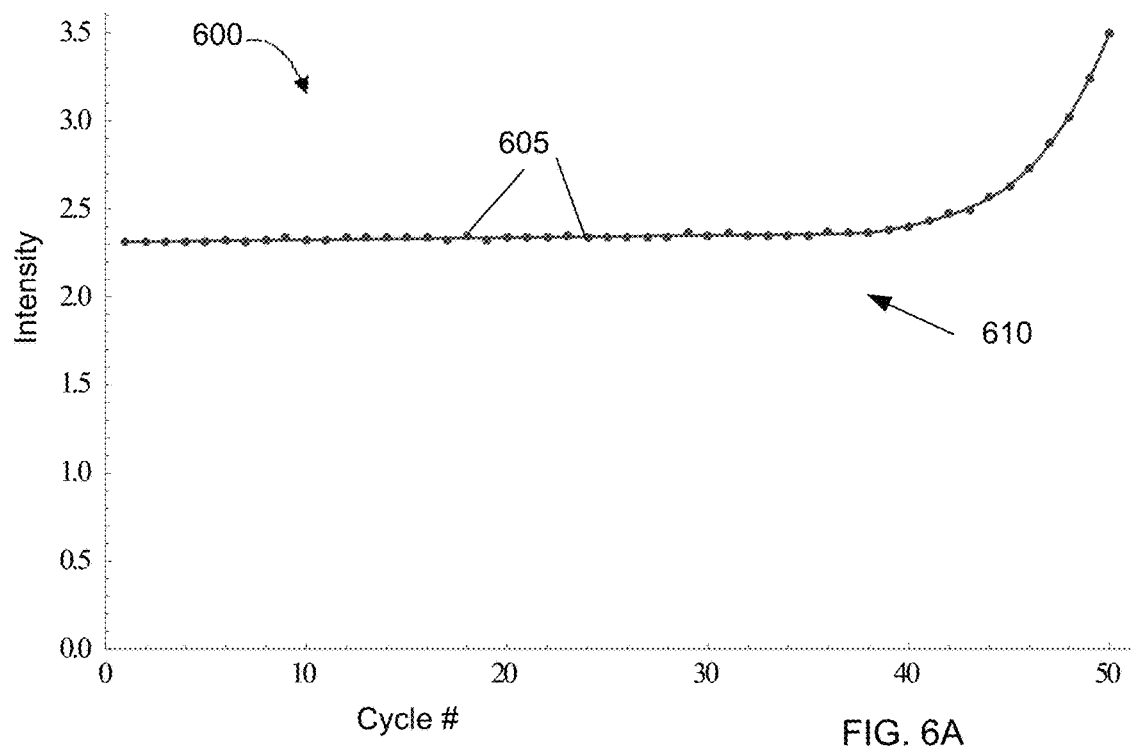
FIG. 6A shows a plot 600 of PCR data points 605 and function 610 that approximate points 605 according to embodiments of the present invention.
Figure 6B:
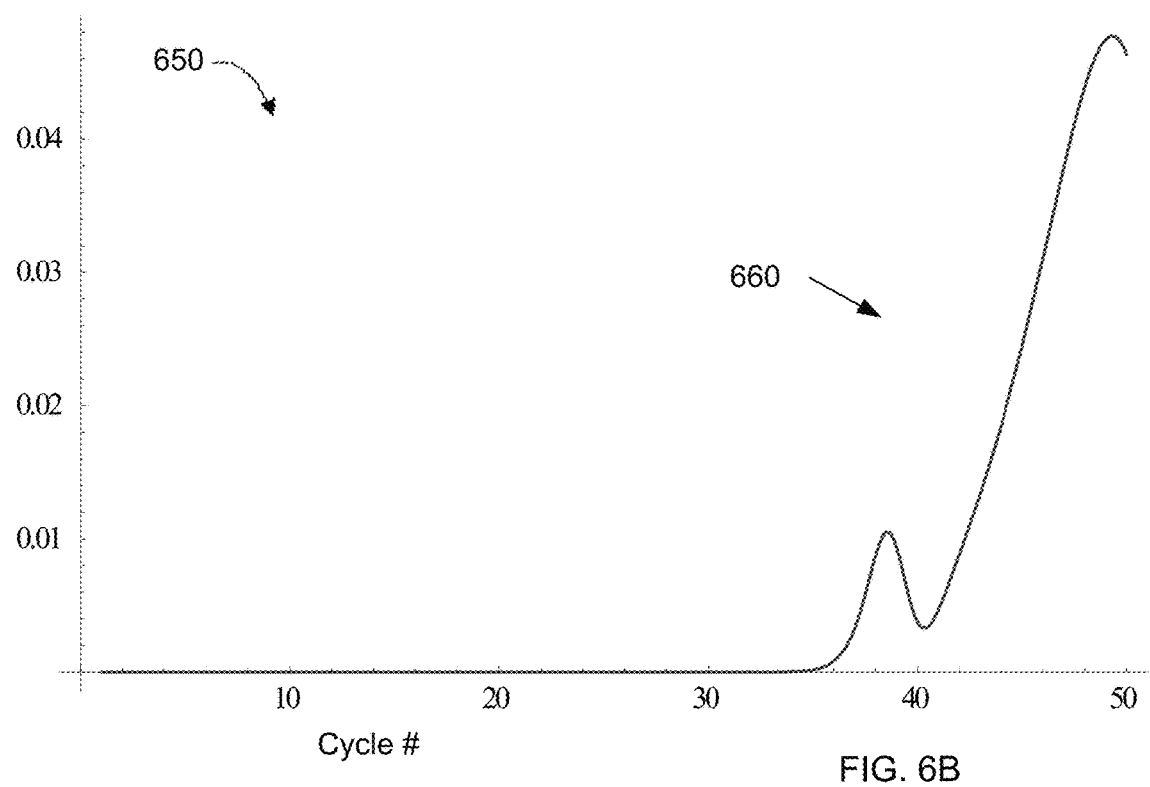
FIG. 6B shows a plot 650 of the second derivative 660 of function 610.

FIG. 6A shows a plot 600 of PCR data points 605 and function 610 that approximate points 605 according to embodiments of the present invention. As shown, function 610 was fit using equation (1). FIG. 6B shows a plot 650 of the second derivative 660 of function 610. Plot 650 shows that the second derivative 660 has a second derivative maximum (at 49.31). But, there is no inflection point, as the second derivative does not go through zero after its increase from the baseline. Hence, it is not possible to determine the Ct using the slope at the inflection point.

It is possible to determine a Ct using the second derivative maximum, but the estimate is 49.31, which is the maximum of second derivative 660. Using an intersection of the tangent (i.e. a line tangent to function 610 at cycle 49.31) with the baseline provides Ct=45.53, which is a better estimate than 49.31. Using the tangent line at the maximum of second derivative 660 brings Ct more in line with elbow of function 610.

VI. Calibration Curves

As described above, a calibration curve can be used to determine an initial concentration of a sample using a Ct value. Such calibration curves are normally presented as a log of concentration, and give a linear plot. With the value of Ct one can then obtain the corresponding initial concentration on a log scale. The following calibration data is for an assay covering a range of nine logs (i.e. $10^9$ range in concentration).

Figure 7A:
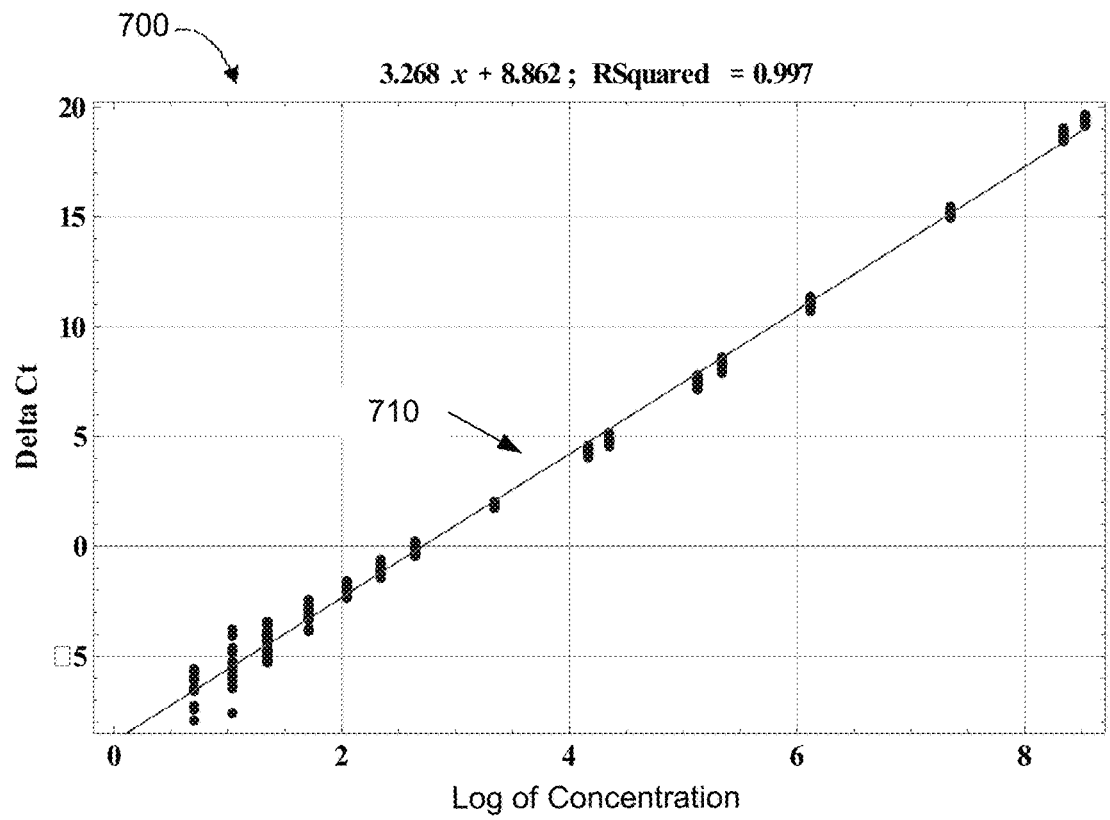
FIG. 7A shows a plot 700 of a calibration curve 710 determined according to embodiments of the present invention.

FIG. 7A shows a plot 700 of a calibration curve 710 determined according to embodiments of the present invention. The X-axis is the log of concentration and the Y-axis is delta Ct (target Ct minus control Ct), where the control Ct is the Ct measured with a fixed amount of pure species under investigation. Calibration curve 710 has the linear form of 3.268x+8.862. It is seen in FIG. 7A that calibration curve 760 shows near perfect linearity of $R^2=0.997$ when delta Ct is plotted verses the logarithm of concentration.

Figure 7B:
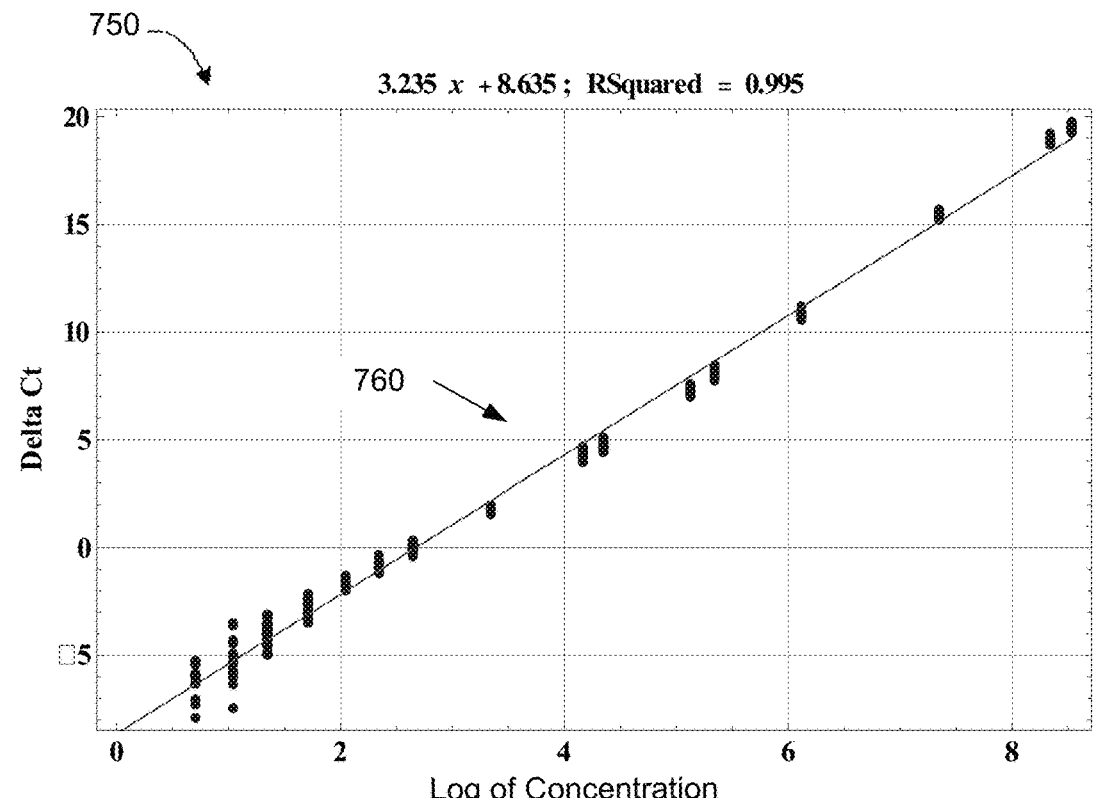
FIG. 7B shows an analogous plot 750 of a calibration curve 760 determined using the second derivative maximum.

For comparison, FIG. 7B shows an analogous plot 750 of a calibration curve 760 determined using the second derivative maximum. Calibration curve 760 has the linear form of 3.235x+8.635, with an $R^2$ of 0.995. Thus, the embodiments used for plot 700 have even slightly better linearity than a technique using the second derivative maximum. Additionally, an advantage over using the maximum of the second derivative as the Ct value for non-parabolic curves is a smaller and more realistic Ct value.

VII. Correlation to Expected Ct

As a further check on the accuracy of embodiment of the present invention, the correlation of the of the measured Ct is compared to an expected Ct. The expected Ct is determined by what a researcher would estimate visually, e.g., just when the curve is rising above the baseline.

Figure 8A:
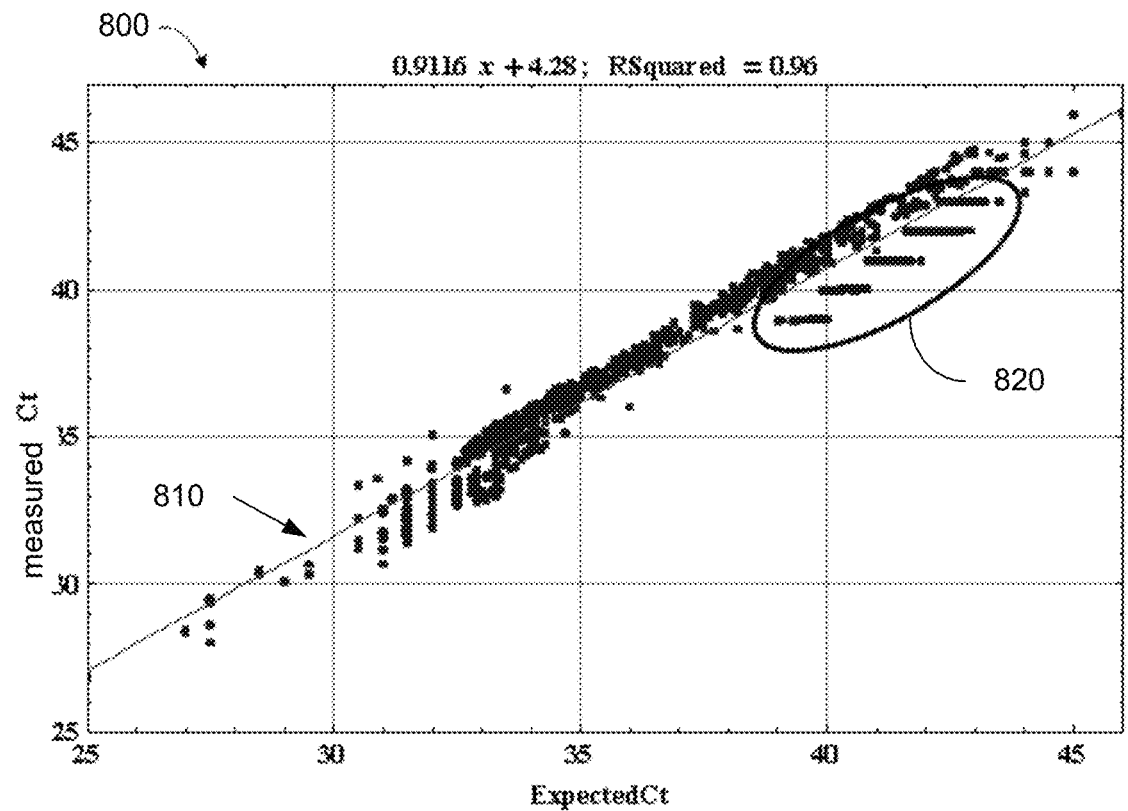
FIG. 8A shows a plot 800 of a correlation line 810 between the measured Ct using the second derivative maximum, as well as a parabolic method for parabolic curves and expected Ct.

FIG. 8A shows a plot 800 of a correlation line 810 between the measured Ct using the second derivative maximum and the expected Ct. A parabolic method (U.S. Pat. No. 8,219,366) was used for parabolic curves. In the area 820 highlighted in an oval, these horizontal data points are the result of the implementation of the parabolic-specific method, which gives decreased linearity. Each data point corresponds to the measured Ct value and the expected Ct value of a PCR curve. Correlation line 810 is a linear fit to the data and has the form 0.9116x+4.28. If there was perfect correlation then line would have slope 1 and 0 y-intercept and $R^2$ of one. Here, $R^2$ equals 0.96, as shown in plot 800. Also, the calculated Ct values are generally two Ct values higher than the expected Ct. The difference in two Ct values can be seen by looking at the correlation line being at measured Ct 27 when the expected the expected Ct is 25.

Figure 8B:
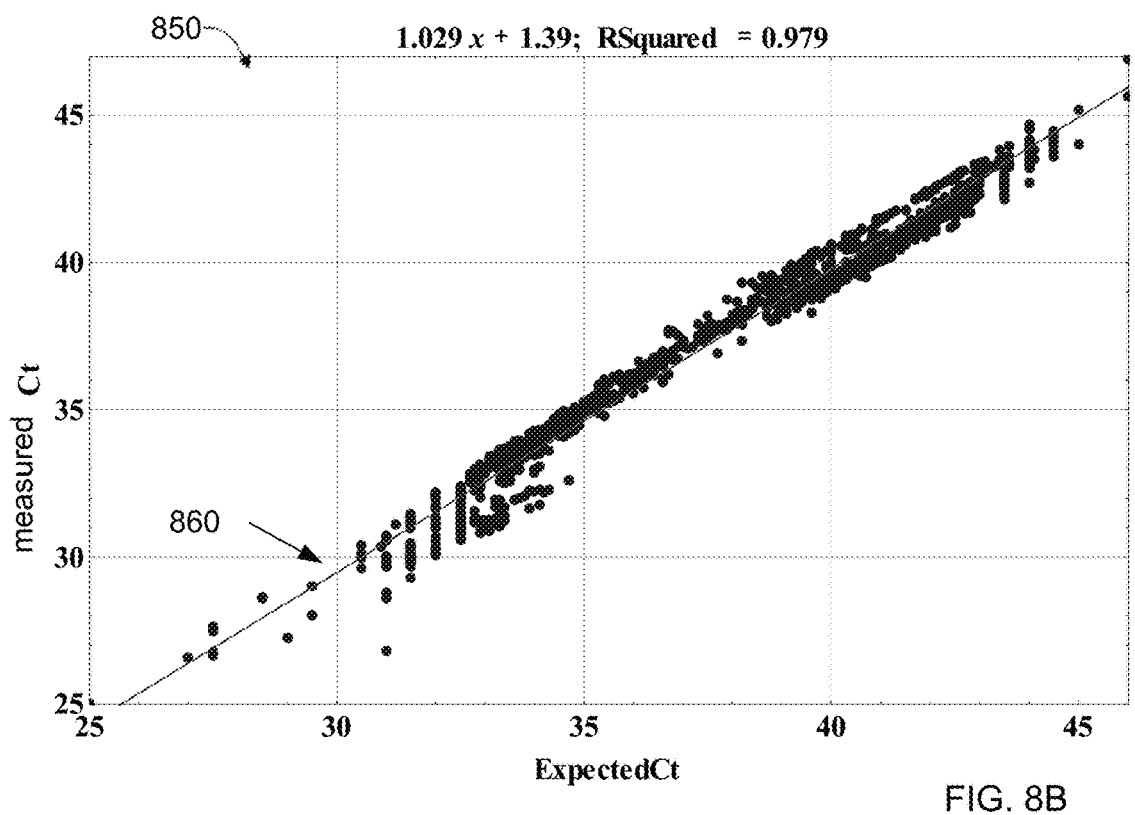
FIG. 8B shows a plot 850 of a correlation line 860 between the measured Ct using an embodiment of the present invention and the expected Ct.

FIG. 8B shows a plot 850 of a correlation line 860 between the measured Ct using an embodiment of the present invention and the expected Ct. A parabolic method was not used for any of the data points. Correlation line 860 is a linear fit to the data and has the form 1.029x+1.39. The linear fit is better with an $R^2$ of 0.98 vs. 0.96. Also, it is seen that there is minimal offset between expected Ct and calculated Ct. Furthermore, the slope is very close to 1 (1.03 vs. 0.91). This demonstrates that calculating the Ct using embodiment of this invention on PCR curves that are sigmoidal and parabolic is superior to calculating Ct values with the second derivative maximum for sigmoidal and switching to a different technique for parabolic curves.

VIII. Comparisons to Baseline Subtraction with Division

Embodiments of the present invention also compare favorably to the baseline subtraction with division method using an AFL (arbitrary fluorescence value). In the AFL method, one subtracts out baseline from the sigmoidal functional fit, and divide by the intercept of the baseline. The Ct is determined by the cycle when the result hits the AFL threshold.

Figure 9:
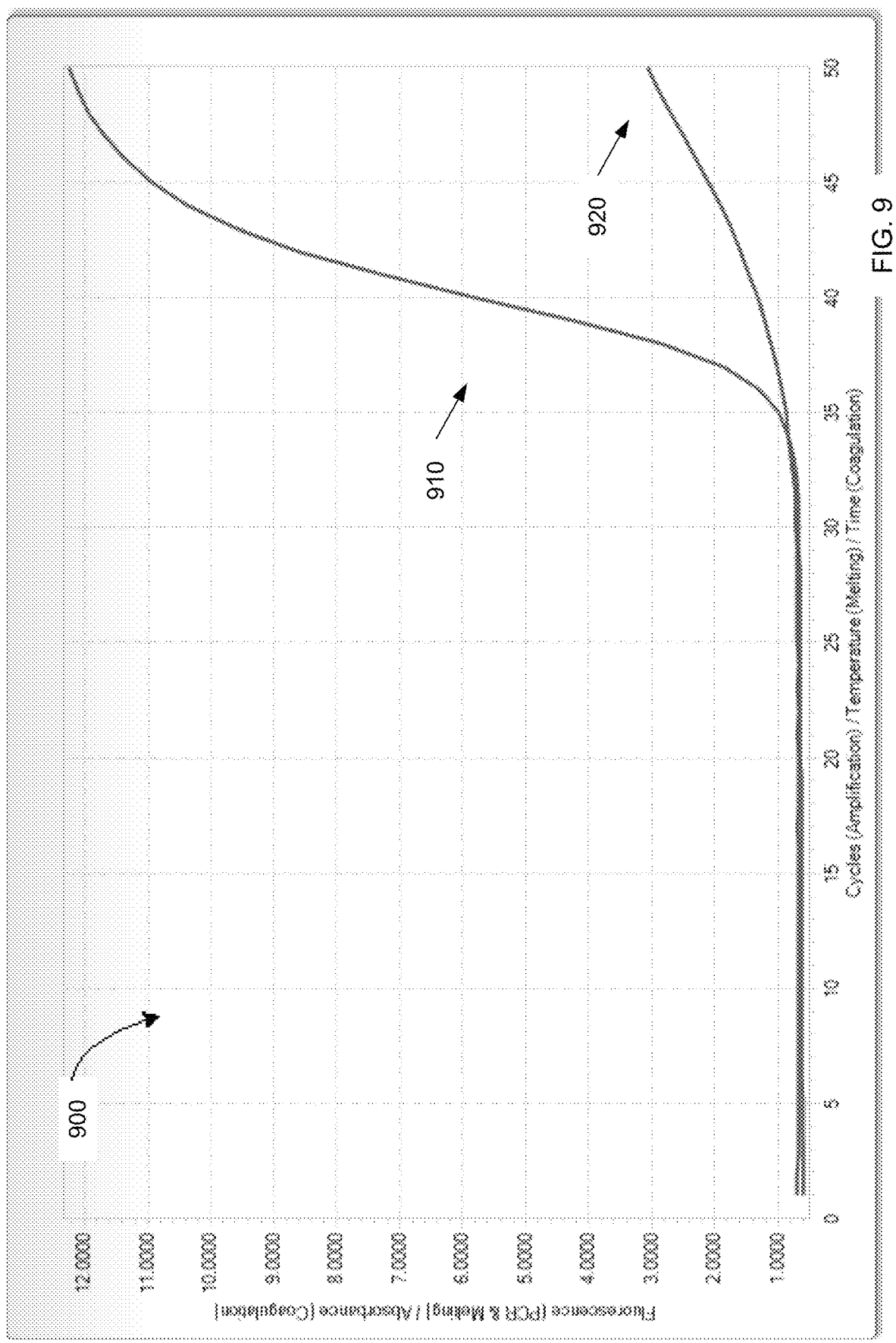
FIG. 9 shows a plot 900 of two raw data curves 910 and 920.

FIG. 9 shows a plot 900 of two raw data curves 910 and 920. In both cases, the expected Ct value is Ct=36. The Ct values calculated using the Baseline Subtraction with Division are 35.03 for curve 910 and 37.06 for curve 920. The Ct using embodiments of the present invention gives 35.86 for curve 910 and 35.43 for curve 920. As one can see, embodiments of the present invention give better agreement to the expected Ct value (36). Additionally, the values 35.86 and 35.43 are closer to each other, thereby providing greater precision.

IX. Computer System

Figure 10:
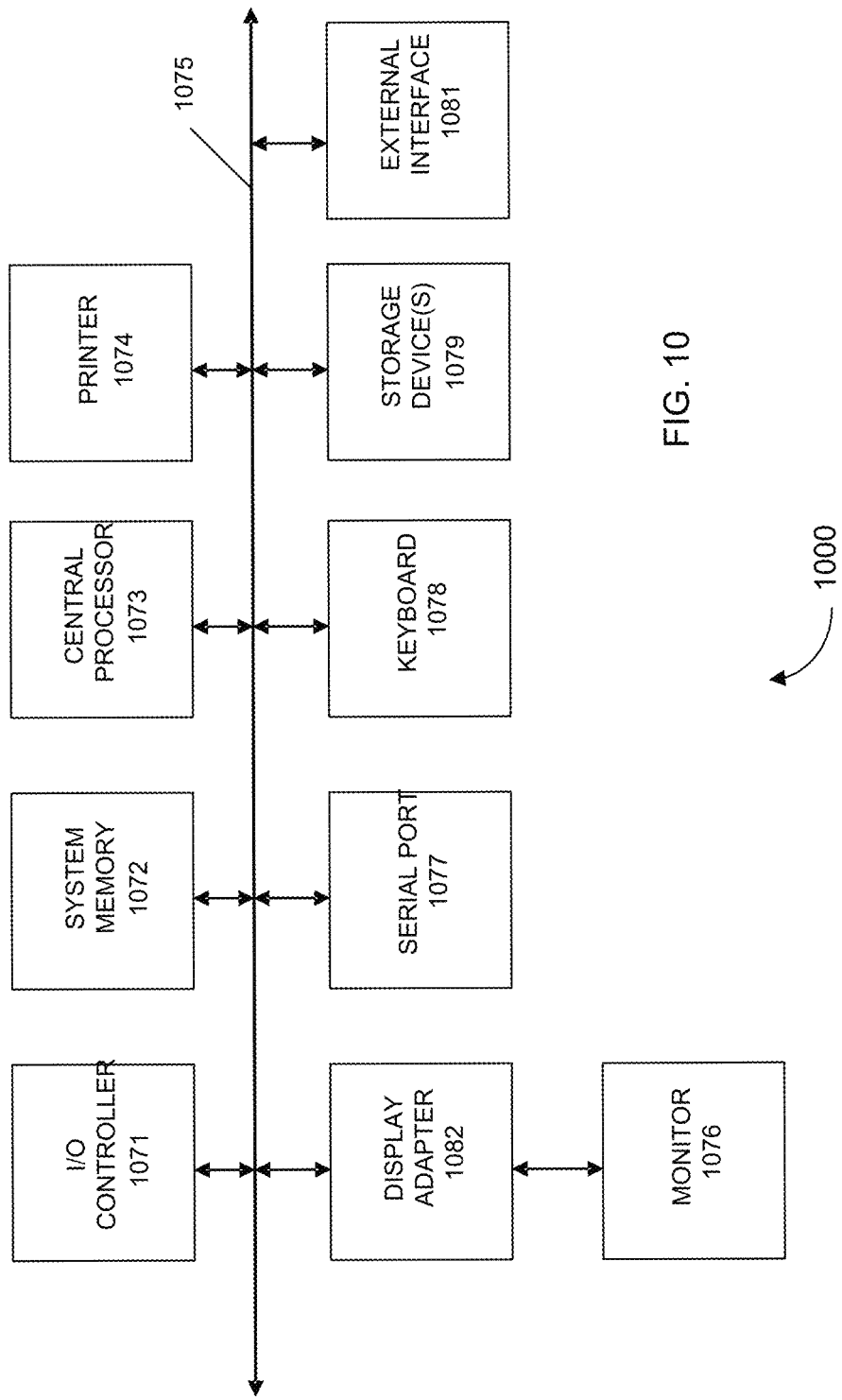
FIG. 10 shows a block diagram of an example computer system 1200 usable with system and methods according to embodiments of the present invention.

Any of the computer systems mentioned herein may utilize any suitable number of subsystems. Examples of such subsystems are shown in FIG. 10 in computer apparatus 1000. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 10 are interconnected via a system bus 1075. Additional subsystems such as a printer 1074, keyboard 1078, storage device(s) 1079, monitor 1076, which is coupled to display adapter 1082, and others are shown. Peripherals and input/output (I/O) devices, which couple to I/O controller 1071, can be connected to the computer system by any number of means known in the art, such as serial port 1077. For example, serial port 1077 or external interface 1081 (e.g. Ethernet, Wi-Fi, etc.) can be used to connect computer system 1000 to a wide area network such as the Internet, a mouse input device, or a scanner. The interconnection via system bus 1075 allows the central processor 1073 to communicate with each subsystem and to control the execution of instructions from system memory 1072 or the storage device(s) 1079 (e.g., a fixed disk), as well as the exchange of information between subsystems. The system memory 1072 and/or the storage device(s) 1079 may embody a computer readable medium. Any of the values mentioned herein can be output from one component to another component and can be output to the user.

A computer system can include a plurality of the same components or subsystems, e.g., connected together by external interface 1081 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned here are incorporated by reference in their entirety for all purposes. None is admitted to be prior art.

What is claimed is:

1. A method of detecting a target analyte in a biological sample, the method comprising:
   detecting signal strengths of signals from a polymerase chain reaction (PCR) system, the signals generated by performing a plurality of growth cycles of a PCR growth process for the biological sample in the PCR system;
   generating a dataset representing a growth curve for the PCR growth process based on the detected signal strengths, the dataset including a plurality of data points, each data point having a pair of coordinate values that includes a cycle number and a signal strength of the PCR growth process at the cycle number, the growth curve including a linear baseline region and a nonlinear region after the baseline region, wherein the nonlinear region includes an exponential increase;
   creating a function that approximates the dataset by adjusting parameters of the function to fit the dataset;
   determining a baseline in the linear baseline region of the growth curve, wherein the baseline is linear;
   identifying a first point of the function where a maximum in a second derivative of the function occurs;
   determining a tangent line that is tangent to the function at the first point;
   identifying an intersection point of the tangent line and the baseline;
   identifying a cycle number of the intersection point representing a cycle threshold value Ct of the PCR growth process for the biological sample; and
   determining a quantity of the target analyte in the biological sample based on the cycle threshold value Ct.

2. The method of claim 1, wherein:
   the first point has a cycle number xval and a signal strength yval; and
   determining the tangent line includes determining a slope slp of the function at {xval,yval} to obtain the tangent line as yval+slp(x−xval), where x is cycle number.

3. The method of claim 2, wherein:
   determining the baseline includes determining a linear function ax+b; and
   identifying the intersection point of the tangent line and the baseline includes solving the following equation for x:

$$(a+bx)=yval+slp(x-xval).$$

4. The method of claim 1, wherein the function includes a double sigmoidal function.

5. The method of claim 4, wherein the double sigmoidal function is characterized by an equation:

$$a + bx + \frac{c}{(1 + \text{Exp}[-d(x-e)]) \cdot (1 + \text{Exp}[-f(x-g)])}.$$

6. The method of claim 1, wherein the target analyte includes a target nucleic acid.

7. The method of claim 6, wherein detecting the signal strengths of the signals generated in the plurality of growth cycles of the PCR growth process for the biological sample includes:

amplifying the target nucleic acid in a repetitive series of cycles of denaturation, primer annealing, and primer extension in a presence of a polymerase; and measuring the signal strengths of the signals generated using fluorescent probes or markers.

8. The method of claim 1, wherein the nonlinear region of the growth curve includes a parabolic curve.

9. The method of claim 8, wherein a second derivative of the parabolic curve does not go through zero.

10. The method of claim 1, further comprising:

removing a portion of the data points before creating the function.

11. A computer product comprising a non-transitory computer readable medium storing a plurality of instructions that, when executed, control a computer system to detecting a target analyte in a biological sample, the instructions comprising:

obtaining a dataset representing a growth curve measured from a polymerase chain reaction (PCR) growth process for the biological sample in a PCR system, the dataset including a plurality of data points, each data point having a pair of coordinate values that includes a cycle number and a signal strength of the PCR growth process at the cycle number, the growth curve including a linear baseline region and a nonlinear region after the baseline region, wherein the nonlinear region includes an exponential increase;

creating a function that approximates the dataset by adjusting parameters of the function to fit the dataset;

determining a baseline in the linear baseline region of the growth curve, wherein the baseline is linear;

identifying a first point of the function where a maximum in a second derivative of the function occurs;

determining a tangent line that is tangent to the function at the first point;

identifying an intersection point of the tangent line and the baseline;

identifying a cycle number of the intersection point representing a cycle threshold value Ct of the PCR growth process for the biological sample; and determining a quantity of the target analyte in the biological sample based on the cycle threshold value Ct.

12. The computer product of claim 11, wherein:

the first point has a cycle number xval and a signal strength yval; and determining the tangent line includes determining a slope slp of the function at {xval,yval} to obtain the tangent line as yval+slp(x−xval), where x is cycle number.

13. The computer product of claim 12, wherein:

determining the baseline includes determining a linear function ax+b; and identifying the intersection point of the tangent line and the baseline includes solving the following equation for x:

$(a+bx)=yval+slp(x-xval)$.

14. The computer product of claim 11, wherein the function includes a double sigmoidal function.

15. The computer product of claim 14, wherein the double sigmoidal function is characterized by an equation:

$$a + bx + \frac{c}{(1 + \text{Exp}[-d(x - e)]) \cdot (1 + \text{Exp}[-f(x - g)])}.$$

16. The computer product of claim 11, wherein the nonlinear region of the growth curve includes a parabolic curve.

17. The computer product of claim 16, wherein a second derivative of the parabolic curve does not go through zero.

18. A Polymerase Chain Reaction (PCR) system, comprising:

a PCR data acquiring device configured to obtain a dataset representing a growth curve of PCR amplification for a biological sample, the dataset including a plurality of data points, each data point having a pair of coordinate values that includes a cycle number and a signal strength of the PCR amplification at the cycle number, wherein the growth curve includes a linear baseline region and a nonlinear region after the baseline region, wherein the nonlinear region includes an exponential increase; and a computer system configured to process the dataset to detect a target analyte in the biological sample by:

receiving the dataset representing the growth curve from the PCR data acquiring device;

creating a function that approximates the dataset by adjusting parameters of the function to fit the dataset;

determining a baseline in the linear baseline region of the growth curve, wherein the baseline is linear;

identifying a first point of the function where a maximum in a second derivative of the function occurs;

determining a tangent line that is tangent to the function at the first point;

identifying an intersection point of the tangent line and the baseline;

identifying a cycle number of the intersection point representing a cycle threshold value Ct of the growth curve of the PCR amplification for the biological sample; and determining a quantity of the target analyte in the biological sample based on the cycle threshold value Ct.

19. The PCR system of claim 18, wherein:

the first point has a cycle number xval and a signal strength yval;

determining the tangent line includes determining a slope slp of the function at {xval,yval} to obtain the tangent line as yval+slp(x−xval), where x is cycle number;

the baseline is characterized by a functional ax+b; and identifying the intersection point of the tangent line and the baseline includes solving the following equation for x:

$(a+bx)=yval+slp(x-xval)$.

20. The PCR system of claim 18, wherein:

the function includes a double sigmoidal function; and the double sigmoidal function is characterized by an equation:

$$a + bx + \frac{c}{(1 + \text{Exp}[-d(x - e)]) \cdot (1 + \text{Exp}[-f(x - g)])}.$$

* * * * *